(12) United States Patent
Gordon et al.

(10) Patent No.: US 6,277,369 B1
(45) Date of Patent: *Aug. 21, 2001

(54) FACTOR 1X DELIVERY METHOD USING BONE MARROW-DERIVED CELLS

(75) Inventors: Erlinda M. Gordon, Glendale; W. French Anderson, San Marino; Frederick L. Hall, Glendale, all of CA (US)

(73) Assignee: University of Southern California, Los Angeles, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/528,696

(22) Filed: Mar. 17, 2000

Related U.S. Application Data

(62) Division of application No. 08/747,514, filed on Nov. 12, 1996, now Pat. No. 6,063,593.

(51) Int. Cl.⁷ .......................... A61K 48/00; A01N 63/00; C12P 21/04; C12N 15/00
(52) U.S. Cl. .................... 424/93.21; 424/93.2; 435/69.7; 435/325
(58) Field of Search .................................. 435/69.1, 69.6, 435/70.4, 402, 320.1, 325, 370; 424/93.2, 93.21

(56) References Cited

U.S. PATENT DOCUMENTS 6,063,593 * 5/2000 Gordon et al. ...................... 435/69.1

OTHER PUBLICATIONS

Hao et al (1995) Human Gene Therapy 7, 873–880.*
Crystal (1997) Science 270, 404–410.*

* cited by examiner

*Primary Examiner*—Deborah Crouch
(74) *Attorney, Agent, or Firm*—Fish & Richarson PC

(57) ABSTRACT

A method for expressing a recombinant protein from bone marrow-derived cells comprises the steps of treating the bone marrow-derived cells in vitro with a TGFβ1 protein, which selects a population of the cells for further treatment. The selected cells can then be expanded, after which a gene encoding a therapeutic protein can be inserted into the expanded cells and thereafter express the therapeutic protein. The transduced cells can then be introduced into a mammal to produce a therapeutic result.

4 Claims, 4 Drawing Sheets

VWF-TGF-β Fusion protein

Trp-Arg-Glu-Pro-Ser-Phe-Met-Ala-Leu-Ser (HIS)$_6$ — TGF-β1

↑ Proteases site

FIG. 1

DMEM
- □ 10% FBS
- ◇ 5% FBS
- ○ 3% FBS
- △ 2% FBS
- ▽ 1% FBS

CELL COUNT, $10^4$ vs TIME, DAYS

FIG. 2

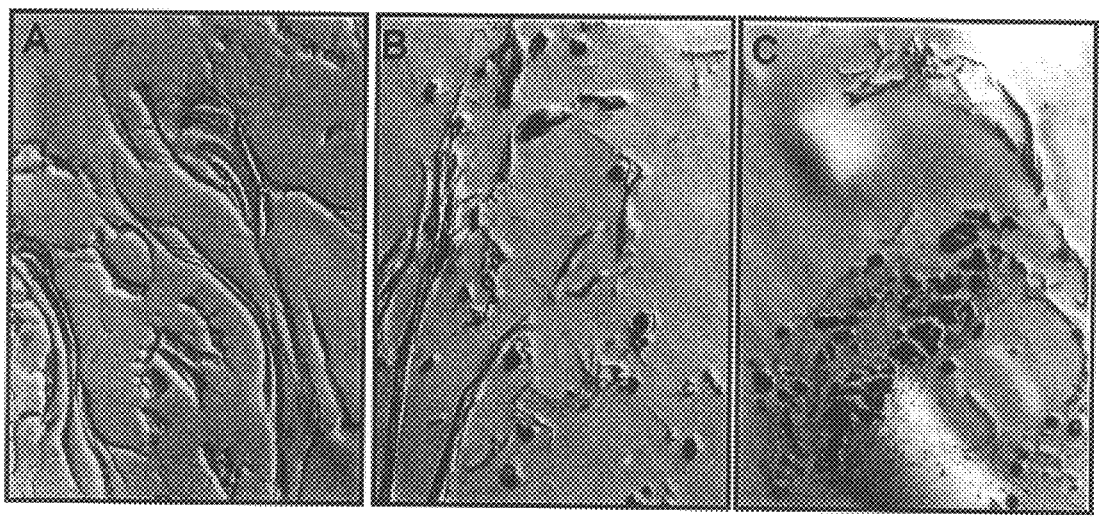
FIG. 3A   FIG. 3B   FIG. 3C
FIG. 5A   FIG. 5B
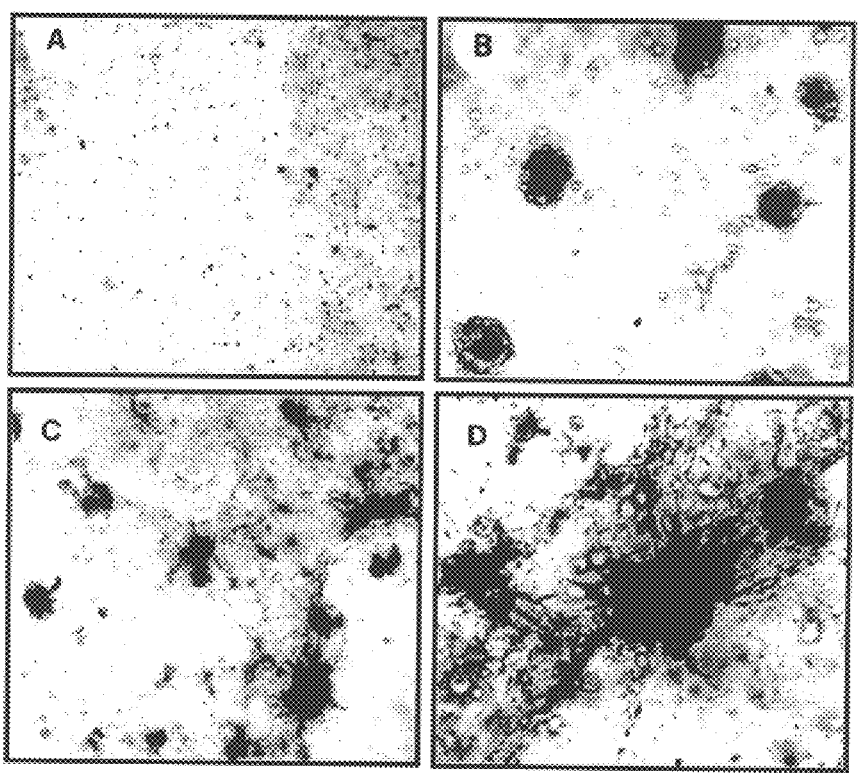
FIG. 5C   FIG. 5D

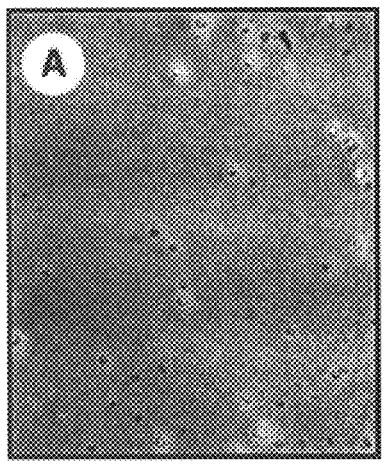 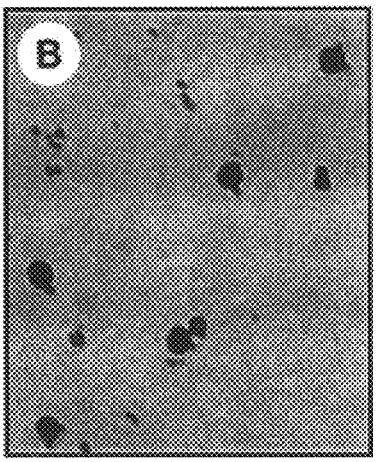 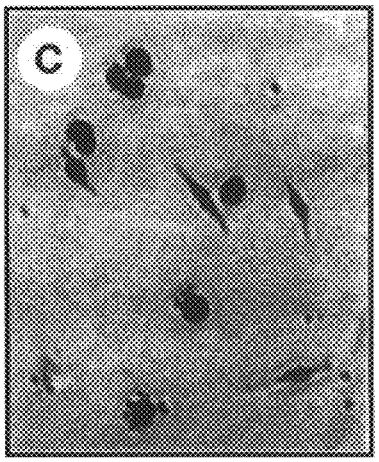
*FIG. 6A*  *FIG. 6B*  *FIG. 6C*
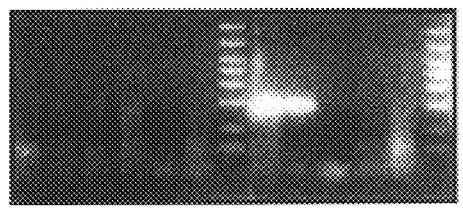
*FIG. 7*

FACTOR 1X DELIVERY METHOD USING BONE MARROW-DERIVED CELLS

This application is a Division of Ser. No. 08/747,514 filed Nov. 12, 1996 U.S. Pat. No. 6,063,593.

FIELD OF THE INVENTION

The present invention relates to the use of bone marrow-derived cells as vehicles for gene transfer. More particularly, this invention relates to the use of a transforming growth factor β1 (TGFβ1) protein for selecting from bone marrow-derived cells a population of cells that are responsive to the TGFβ1 protein. The selected cells can thereafter be used as vehicles for transferring genes encoding a therapeutic protein to a mammal, including humans.

BACKGROUND OF THE INVENTION

Mesenchymal stem cells give rise to the progenitors of many differentiated phenotypes including osteocytes, chrondocytes, myocytes, adipocytes, fibroblasts, and marrow stromal cells. Certain mesenchymal progenitor cells are capable of self-renewal and undergo expansion in the presence of transforming growth factor β1 (TGFβ1), a pleotropic cytokine with autocrine and paracrine functions.

Transforming growth factor β1 (TGFβ1), a 25 KDa peptide found abundantly in platelets and bone, released in response to tissue injury, is becoming an increasingly important tool for immunomodulation, wound healing, and tissue repair. TGFβ is also a chemoattractant for cells of mesenchymal origin, and as such, recruits fibroblasts to the site of injury, stimulates angiogenesis and de novo synthesis of extracellular matrix proteins in concert with the up-regulation of inhibitors of matrix degradation. See Roberts A. B., Sporn M. B.: *The Transforming Growth Factor-βs*, pp. 420–472 (1990). TGFβ1 and TGFβ2 are potent immunoregulatory agents, suppressing the proliferation and function of T and B lymphocytes in vitro (Id.) and in vivo (See Wrann M, et al., "T Cell Suppressor Factor from Human Glioblastoma Cells Is a 12.5 KD Protein Closely Relating to Transforming Growth Factor-beta," *EMP. J.* 6:1633–36 (1987)). Hence, TGFβ appears to play a crucial role in clinically relevant disorders of immune surveillance, tissue regeneration, and repair. Moreover, repair after tissue injury such as burns, myocardial infarction, cerebral ischemia and trauma, as well as surgical wound healing, may be accelerated by a single systemic infusion or local application of this peptide growth factor. See Beck S. L., et al., "TGF-β1 Induces Bone Closure of Skull Defects," *J. Bone Mineral Res.* 6(1991). The therapeutic effects of TGFβ administration may be augmented and/or prolonged by its pronounced autocrine and paracrine functions.

U.S. Pat. No. 5,486,359 (Caplan et al.) is directed to isolated human mesenchymal stem cells, and a method for their isolation, purification, and culturing. Caplan et al. also describe methods for characterizing and using the purified mesenchymal stem cells for research diagnostic and therapeutic purposes.

Heretofore, TGFβ1 has not been demonstrated to function as a survival factor, as opposed to a growth (proliferation) factor.

SUMMARY OF THE INVENTION

The present invention is directed to a method for expressing a recombinant protein from bone-marrow derived cells, comprising the steps of treating the bone marrow-derived cells in vitro with a TGFβ1 protein, which selects from the cells a population of cells that are responsive to the TGFβ1 protein. The selected calls can be thereafter expanded in the cell culture, after which the cells can be transduced with a DNA segment encoding a therapeutic protein to cause the cells to express the therapeutic protein. The transduced cells can then be introduced into a recipient to produce a therapeutic result.

Bone marrow-derived cells for use in the present invention include mesenchymal stem cells and differentiated mesenchymal cells, such as stromal cells.

In a preferred embodiment, the TGFβ1 protein is a TGFβ1 fusion protein comprising an extracellular matrix binding site, which is preferably a collagen binding site. The extracellular matrix binding site of the TGFβ1 fusion protein can then be used to target the TGFβ1 fusion protein to an extracellular matrix, such as collagen.

In another aspect, the present invention is directed to a gene therapy method comprising the steps of capturing TGFβ1-responsive, bone marrow-derived cells under low serum conditions in a collagen matrix impregnated with a TGFβ1 fusion protein comprising a von Willebrand's factor-derived collagen binding site (TGFβ1-vWF) which targets the TGFβ1 fusion protein to the collagen matrix. The captured cells then can be expanded in the cell culture to form differentiated cell colonies. These expanded cell colonies can then be transduced in vitro with a viral vector comprising a gene encoding a therapeutic protein, wherein the gene is expressed to produce the therapeutic protein. The transduced cells can thereafter be introduced into a mammal, such as a human, to produce a therapeutic result.

In a particular embodiment of the invention, it has been discovered that mesenchymal progenitor cells isolated with a TGFβ1-vWF fusion protein, expanded in culture, and transduced with a retroviral vector containing the gene encoding factor IX expressed significant levels of factor IX protein. Moreover, when the transduced cells were transplanted into immunocompetent mice, the human factor IX transgene was expressed in vivo.

BRIEF DESCRIPTION OF THE DRAWINGS

Features, aspects and advantages of the invention will be more fully understood when considered with respect to the following detailed description, appended claims and accompanying drawings where:

FIG. 1 is a schematic representation of the genetically engineered TGFβ1-von Willebrand's factor fusion construct. The expressed protein contains a histidine purification tag, a protease site, an auxiliary collagen-binding decapeptide sequence and the cDNA sequence encoding the mature active fragment of human TGFβ1.

FIG. 2 shows the proliferation of marrow stromal cells in varying concentrations of fetal bovine serum (FBS). The cell number, plotted on the vertical axis, is expressed as a function of the serum concentration (% FBS) over a time period of 6 days, plotted on the horizontal axis.

FIG. 3 contains gel photographs showing hematoxylin-eosin (H & E) stained sections of control, untreated collagen pads in FIG. 3(*a*), and TGFβ1-vWF-treated collagen pads in FIGS. 3(*b*) and 3(*c*) after removal from bone marrow cultures after 8 days.

in FIG. 4(*b*), survival of a primitive population of blastoid cells in collagen gels augmented by a recombinant, collagen-binding TGFβ1 fusion protein.

FIG. 5 contains gel photographs showing the differentiation of collagen/TGFβ1-captured stem cells into an osteogenic lineage. FIG. 5(a) shows control bone marrow aspirates cultured in collagen gels, in the absence of the recombinant TGFβ1 fusion protein, while FIG. 5(b) shows the expansion of osteogenic colonies, in the presence of the recombinant TGFβ1 fusion protein and after subsequent culturing in the presence of osteoinductive factors (dexamethasone, vitamin C and β-glycerophosphate).

FIG. 5(c) shows the formation of osteogenic "tissues" in the presence of the TGFβ1 fusion protein and osteoinductive factors. FIG. 5(d) is an enlargement of FIG. 5(c).

FIG. 6 are photographs of gels showing in FIG. 6(a), control bone marrow aspirates cultured in collagen-coated wells, in the absence of TGFβ1-vWF; in FIG. 6(b), the capture of a population of blastoid precursor cells in collagen-coated wells impregnated with TGFβ1-vWF; and in FIG. 6(c), transplanted, marrow mesenchymal cells following capture and expansion in the presence of TGFβ1-vWF, reconstitution with serum, and transduction with the LIXSNL vector.

FIG. 7 shows reverse transcriptase-polymerase chain reaction-based (RT-PCR-based) detection of unique human factor IX sequences in the bone marrow (Lane 2) and lung (Lane 3) of recipient mice twenty-eight days after transplantation of factor IX, vector-transduced mesenchymal progenitor cells. The mice were sacrificed for RT-PCR detection of human factor IX sequences in various mouse organs. Positive bands identifying human factor IX cDNA sequences (Lanes 8 and 9) are seen in a 180 bp region of non-homology to mouse factor IX cDNA sequences. The samples run from various murine tissues are as follows:

Figure 4A:
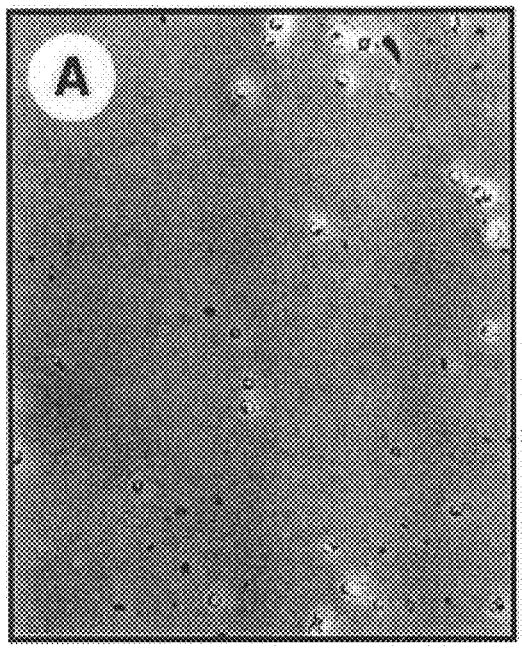
FIG. 4 contains gel photographs demonstrating in FIG. 4(*a*), bone marrow aspirates cultured in serum-poor medium which exhibit cell degeneration and cell death.
in FIG. 4(c), expansion of captured stem cells after selection, in the presence of additional serum factors; and in FIG. 4(d), formation of colonies of expanded stem cells, revealing stromal/fibroblastic derivatives.

Lane 1, LIXSNL/liver; Lane 2, LIXSNL/bone marrow; Lane 3, LIXSNL/lung; Lane 4, LXSNL/liver; Lane 5, LXSNL/bone marrow; Lane 6, LIXSNL/kidney; Lane 7, 1 Kb Marker; Lanes 8 and 9, human liver; Lane 10, blank; Lane 11, LIXSNL/spleen; Lane 12, LXSNL/kidney.

DETAILED DESCRIPTION OF THE INVENTION

As indicated above, the present invention relates to the use of bone marrow-derived cells as cellular vehicles for gene transfer. In particular, the present invention demonstrates that bone marrow-derived, mesenchymal progenitor cells can be selected and expanded by virtue of their intrinsic physiological responses to TGFβ1. The present invention further demonstrates the utility of these treated cells for conducting gene therapy approaches in mammals, including humans.

The present invention is directed to a method for expressing a recombinant protein from bone marrow-derived cells comprising the steps of treating bone marrow-derived cells in vitro with a TGFβ1 protein, thereby selecting from the cells a population of cells that are responsive to the TGFβ1 protein. The selected cells can be then expanded in the cell culture. A DNA segment encoding a therapeutic protein can be then inserted into the expanded cells, to cause the cells to express the therapeutic protein.

In a preferred embodiment, the TGFβ1 protein used for treating the bone marrow-derived cells in vitro is a TGFβ1 fusion protein comprising an extracellular matrix binding site. The extracellular matrix binding site enables the TGFβ1 fusion protein to bind to an extracellular matrix, such as a collagen matrix. A preferred extracellular matrix binding site is thus a collagen binding site. Types of collagen matrices include gels and pads. This binding of the TGFβ1 fusion protein to the extracellular matrix permits the capture of TGFβ1-responsive, bone marrow-derived cells in the extracellular matrix.

The bone marrow-derived cells used to carry out the present invention include mesenchymal stem cells, also referred to as TGFβ1-responsive progenitor cells (TRPC), and differentiated bone marrow-derived cells, such as stromal cells.

Introduction of a DNA segment in vitro into bone marrow-derived cells may be accomplished by known procedures, preferably by transduction with a viral vector, most preferably a retroviral vector. Nonviral procedures include electroporation, calcium phosphate mediated transfection, microinjection and proteoliposomes.

The DNA segment introduced into the bone marrow-derived cells in the present method can encode any of a variety of therapeutic proteins. The method of this invention is particularly useful for genetic therapeutic approaches to correcting defects in the thrombosis-hemostasis system. Examples of suitable genes or DNA segments include those that encode human factor IX, factor VIIIc, von Willebrand's factor, tissue plasmogen activator, protein C, protein S and antithrombin III.

The present invention is also directed to a method for providing a mammal with a therapeutically effective amount of a therapeutic protein by introducing TGFβ1-responsive, bone marrow-derived cells into the mammal. The TGFβ1-responsive, bone marrow-derived cells are treated in vitro prior to introduction into the mammal, first, with a TGFβ1 protein to select the TGFβ1-responsive cells from the remainder of cellular components contained in a bone marrow aspirate, and second, to insert into the TGFβ1-responsive cells a DNA segment encoding a therapeutic protein. The transduced cells thereafter will express a therapeutically effective amount of the therapeutic protein in vivo in the mammal.

The present invention also is directed to a gene therapy method comprising the first step of capturing TGFβ1-responsive, bone marrow-derived cells, preferably mesenchymal progenitor cells, under low serum conditions in a collagen matrix (e.g., pads and gels) impregnated with a recombinant TGFβ1-fusion protein comprising a collagen binding site, preferably derived from von Willebrand's factor, which targets the TGFβ1 protein to the collagen matrix and prolongs its biological half-life. See Tuan T. L., et al., "Engineering, Expression and Renaturation of Targeted TGF-beta Fusion Proteins," *Conn. Tiss. Res.* 34:1–9 (1996). Engineered TGFβ1 fusion proteins incorporating the collagen binding site which is fused with an active fragment of the TGFβ1 protein, as shown in FIG. 1, exhibit functional properties that do not exist in nature. See Tuan T. L., et al. These collagen-targeted, TGFβ1-vWF fusion proteins were found to function efficiently in capturing the TGFβ1-responsive, blastoid progenitor cells. TGFβ1 constructs lacking the collagen binding domain were not as efficient.

The gene therapy method of the present invention comprises expanding the TGFβ1-responsive cells to form differentiated cell colonies, followed by the step of transducing the expanded cells in vitro using known gene transfer procedures, including viral-mediated, and preferably retroviral-mediated, gene transfer. In a preferred embodiment, additional TGFβ1, preferably from a purified source, is added to the cells during the capture and expansion steps. The transduced cells can then express the therapeutic protein.

The gene therapy method of the present invention also comprises the step of introducing the transduced cells into a mammal to produce a therapeutic result. More specifically, and as set forth in more detail below, the present invention demonstrates the utility of TGFβ-vWF impregnated collagen matrices for isolating novel target cells as vehicles for carrying out ex vivo gene therapy.

To optimize the cell culture conditions for effecting the ex vivo selection of TGFβ1-responsive progenitor cells, varying concentrations of fetal bovine serum (FBS) were added to bone marrow stromal cells grown in Dulbecco's Minimum Essential Medium (DMEM) for 6 days. FIG. 2 shows a characteristic decrease in cell number observed at 24 hours, followed by a serum-dependent increase in cell counts over time. No rise in cell count was observed in cultures supplemented with 1% FBS or less, while cultures supplemented with concentrations greater than 1% FBS showed a progressive recovery after a lag period of about 3 days. Based on the above, 1% and 0.5% FBS were used as minimal concentrations of serum for developing conditions favorable for the survival of TGFβ1-responsive cells.

FIG. 3 shows hematoxylineosin stained sections of collagen pads. Specifically, FIG. 3(a) shows control, untreated pads, while FIGS. 3(b) and 3(c) show TGFβ1-vWF treated pads removed from bone marrow cultures after 8 days. The untreated collagen pads showed a uniform absence of cellular elements, whereas the sections of TGFβ1-vWF treated pads revealed a population of small, mononuclear blastoid cells having coarse nuclear chromatin and nucleoli surrounded in some areas by a narrow rim of blue agranular cytoplasm. A pleomorphic population of cells, including blastoid cells and presumptive derivatives, occasionally was noted, as shown in FIG. 3(c). Both types of cells appear to have secreted extracellular matrix proteins de novo. These matrix proteins are distinguishable from the original collagen fibers.

After conducting the above studies using human bone marrow aspirates, cell cultures were observed directly in additional studies wherein the selection (capture) and mitotic expansion of rodent marrow-derived cells cultured in collagen gels were investigated. By comparing FIGS. 4(a) and 4(b), it is shown that maintaining a relatively uniform population of blastoid cells required the presence of TGFβ1-vWF fusion protein within the collagen matrix. As demonstrated by FIG. 4(b), TGFβ1-vWF apparently supported the survival, but not the expansion of these blastoid cells under low serum conditions. However, upon adding 10% FBS to the cell culture, the captured cells began to proliferate, as evidenced by the formation of cell doublets, as shown in FIG. 4(c), and the formation of multicellular colonies, as shown in FIG. 4(d). That the captured blastoid cells had formed from mesenchymal cells was confirmed, as shown in FIG. 5, by adding osteoinductive factors (dexamethasone, vitamin C, and β-glycerophosphate) to the complete growth medium, which induced cytodifferentiation and mineralization of the expanding colonies.

Using a vector containing β-galactosidase gene as a reporter gene, the transduction efficiency observed in both rodent and human TGFβ1-vWF-captured, bone marrow-derived mesenchymal progenitor cells ranged from 20–30%. In comparing gene delivery into TGFβ1-vWF expanded stem cells to that of delivery into differentiated cells having a phenotype of mesenchymal origin, both marrow-derived stem cells and mature stromal cells were transduced with a retroviral vector bearing a human factor IX cDNA (LIXSNL). Table I below shows factor IX production after expanding selected cells in the presence of TGFβ1-vWF fusion protein, followed by transducing the cells with the LIXSNL vector. The cells that were captured and expanded as a result of treatment with collagen-bound TGFβ1-vWF fusion protein produced significant (µg) quantities of factor IX protein per $10^6$ cells.

It also was observed that further supplementing the cell cultures with purified TGFβ1 induced a dramatic (ten-fold) increase in factor IX production

TABLE I

Factor IX Production in Human Marrow Mesenchymal Stem Cells after Expansion with a TGFβ1-vWF Fusion Protein and Retroviral Vector-mediated Gene Transfer

| Experiment | Factor IX µg/$10^6$ cells/day |
|---|---|
| Collagen + TGFβ1-vWF | 5.8 ± 2.6 |
| | n = 4 |
| Collagen + TGFβ1-vWF + TGFβ1 | 53.7 ± 12.5 |
| | n = 4 |
| | p < 0.001 |

* Factor IX antigen was not detected in cultures transduced with the control vector.

The level of factor IX produced by these TGFβ1-stimulated cell cultures was found to be considerably higher than the levels produced by mature cells of mesenchymal origin after retroviral vector-mediated gene transfer alone. However, these stimulated cultures of mesenchymal progenitor cells exhibited relatively low coagulant activity (0.1 mU clotting activity/ng protein), thus suggesting that the cells were biochemically immature and/or, as addressed further below, had not yet developed a competent τ-carboxylation system.

By comparison, a similar transduction efficiency (of about 28%) of the β galactosidase vector in differentiated marrow stromal cells was observed. Table II below shows factor IX production in G418-selected marrow stromal cells following transduction with a vector containing the factor IX gene. The amount of biologically active factor IX secreted in these cultures was proportional to the antigen level, indicating a functional τ-carboxylation system and exhibiting a ratio of native factor IX coagulant activity to antigen consistent with the ratio observed in normal plasma (1 mU clotting activity/5 ng protein). The level of factor IX produced by transduced marrow stromal cells was comparable to the expression levels resulting from human fibroblasts. See Palmer, T. D., et al., "Production of Human Factor IX in Animals by Genetically Modified Skin Fibroblasts: Potential Therapy for Hemophilia B. *Blood* 73:438–445 (1989).

TABLE II

Factor IX Production in Human Marrow Stromal Cells After Retroviral Vector-mediated Gene Transfer and G418 Selection

| Sample Number | Factor IX Antigen µg/$10^6$ cell/day | Factor IX Clotting Activity mU/$10^6$ cells/day |
|---|---|---|
| I | 1/3 | 258.0 |
| II | 0.3 | 52.5 |

TABLE II-continued

Factor IX Production in Human Marrow Stromal
Cells After Retroviral Vector-mediated Gene
Transfer and G418 Selection

| Sample Number | Factor IX Antigen μg/10⁶ cell/day | Factor IX Clotting Activity mU/10⁶ cells/day |
|---|---|---|
| III | 0.3 | 68.0 |
| IV | 0.3 | 60.0 |

\* Tabulated data are the result of duplicate assays. Factor IX antigen and clotting activity were detected in cultures transduced with the control vector.

A pilot study was undertaken to demonstrate the transplantation of transduced progenitor cells, as described above, into inbred mice. As shown in FIG. 6(b), TGFβ1-vWF responsive cells from the bone marrow of B6CBA mice were captured on collagen/TGFβ1-vWF matrices under serum-poor conditions (1% FBS) for 5 days, after which, as shown in FIG. 6(c), the selected cultures were then reconstituted in complete growth medium (D10) for 2 days. The expanded cell cultures were then transduced with the LIXSNL vector in the presence of 8 μg/ml Polybrene. On Day 21, 1×10⁵ cells were infused into the tail vein of recipient mice and blood samples were collected every 7 days from the mouser's tail to assay for factor IX antigen.

At the time of transplantation, the mean factor IX production was found to be 2.8 μg/10⁶ cells/24 hours, with a mean clotting activity of 676 mU/10⁶ cells/24 hours and a clotting activity ratio of 1 mU to 4.2 ng protein (n=3). Injecting LIXSNL-transduced progenitor cells through the tail vein of immunocompetent mice (n=3) produced detectable in vivo levels of human factor IX, specifically, up to 14.6 ng human factor IX/ml plasma at Day 7, 9.7 ng/ml at 2 weeks post-transplantation, followed by decreasing to non-detectable levels by 28 days post-transplantation.

The expected level of factor IX transgene expression was estimated based on the amount of factor IX produced in transduced mouse progenitor cell cultures, measured at the time of transplantation, using the formula:

$$\text{Factor IX level (Expected, ng/ml)} = \frac{\text{\# of transplanted cells} \times \text{factor IX production (ng/cell/24 hr)}}{\text{wt/kg} \times \text{plasma volume (ml)}} \times \frac{t_{\frac{1}{2}}(\text{hrs.})}{24 \text{ hrs.}}$$

wherein the "# of transplanted cells" was 1×10⁵, mean "factor IX production" was 2.8 ug/10⁶ cells per 24 hr, mean "weight (wt)/kg X plasma volume (ml)" was 20 gm for a plasma volume of 1 ml (50 ml/kg), and the half-life (t½) for recombinant factor IX was 24 hr. The mean factor IX plasma levels of 14.6 ng/ml and 9.7 ng/ml observed in three transplanted mice on Days 7 and 14, respectively, closely approximated the predicted level of about 14 ng/ml.

As shown in FIG. 7, human factor IX transcripts were detected by RT-PCR in the bone marrow and lungs of treated animals, but not in liver, kidney or spleen.

The therapeutic implications of the present invention for gene therapy are substantial. In particular, the potential exists for using myo-fibro-osteogenic stem cell technology for fetal gene therapies of muscular dystrophy, connective tissue disorders, lipid storage disorders, and skeletal disorders, as well as hemophilia. Moreover, somatic gene therapy may become the optimal treatment for hemophilia B (coagulation factor IX deficiency).

Moreover, gene therapy for treating hemophilia B may not require precisely regulated expression, nor site-specific gene integration. Whereas factor IX levels as high as 150% are found in healthy individuals, a factor IX level of only 5% would eliminate crippling disease caused by recurrent joint hemorrhaging. Because factor IX normally circulates in plasma, any engineered cell having vascular access that produces sufficient levels of functional factor IX can be a continuous in vivo source, thus obviating the need for repeated transfusions. Mesenchymal progenitor cells, in particular, are an attractive candidate due to their ability to self-renew and differentiate into secretory phenotypes present within the bone marrow.

The present invention will be illustrated in detail in the following examples. These examples are included for illustrative purposes and should not be considered to limit the present invention.

EXAMPLE 1

Production of a Recombinant TGFβ1-vWF Fusion Protein

A prokaryotic expression vector was engineered to produce a tripartite fusion protein, as shown in FIG. 1, consisting of a 6xHis purification tag, an auxiliary von Willebrand factor-derived collagen-binding site, and a cDNA sequence encoding the mature active fragment of human TGFβ1 (TGFβ1-vWF). The method of preparing the TGFβ1l-vWF fusion protein is the subject of co-pending U.S. application Ser. No. 08/465,772, filed Jun. 6, 1995, and incorporated herein by reference. See also Tuan T. L., et al., "Engineering, Expression and Renaturation of Targeted TGF-beta Fusion Proteins," $Conn. Tiss. Res.$ 34:1–9 (1996), also incorporated herein by reference.

A fusion protein expressed from the above vector was isolated and purified to homogeneity from $E.\ coli$ inclusion bodies using nickel chelate chromatography, solubilized with 8M urea, and renatured by oxidative refolding under optimized redox conditions. See U.S. application Ser. No. 08/465,772, incorporated herein by reference; See also Tuan T. L., et al. The biological activity of this construct was then evaluated by in vitro cell proliferation assays, using purified TGFβ1 as a standardized control.

EXAMPLE 2

Preparation of Collagen Matrices

Solid collagen matrices were prepared as described previously by Nimni and co-workers. See Nimni et al., $Biotechnology$ 17:51–82 (1980). Specifically, 5 mm circles were cut from collagen sheets (~1 mm thick) sterilized with 70% ethanol, washed in DMEM, and incubated with TGFβ1-vWF (50 μl/pad; 1 μg) for 2 hours at 37° C. prior to culturing with bone marrow aspirates in 6-well plates.

EXAMPLE 3

Establishing Initial Culture Conditions for Selecting TGFβ1-Responsive Cells

To establish the minimal growth conditions required for selecting TGFβ1-responsive cells, the survival rate of mature adherent stromal cells was monitored by cell counting in cultures containing DMEM supplemented with varying concentrations of FBS (Biowhittaker). The highest concentration of FBS (0.5 to 1%) that afforded a precipitous fall in cell number without significant recovery over 6 days, as demonstrated in FIG. 2, was used as a selection medium for succeeding experiments. Approximately 1×10⁶ normal human bone marrow cells (obtained from the USC Norris Hospital) were plated in each of six-well plates (Falcon) containing 1) TGFβ1-vWF-treated collagen pads, 2) untreated collagen pads (5 mm diameter), or 3) a thin layer of Type 1 rat tail collagen (Becton-Dickenson) pre-incubated with the TGβ1-vWF fusion protein. The cells were grown in minimal serum conditions: 1% FBS in DMEM supplemented with 200 µg/ml ampicillin. The medium was replaced with DMEM-1% FBS every 4 days for 12 days, after which the medium was replenished with 10% FBS prior to transducing the cells. One TGFβ-vWF-treated or untreated collagen pad was removed every 4 days for 12 days, fixed in 10% formalin, embedded in paraffin, sectioned, and stained with hematoxylin-eosin for histologic examination.

EXAMPLE 4

Capture and Expansion of Mesenchymal Progenitor Cells in Collagen Gels

Bone marrow aspirates were obtained from euthanized, one-month old Fisher rats. The femoral, midshaft bone marrow tissue was washed in DMEM containing penicillin (100 U/ml) and streptomycin (100 µg/ml). Bone marrow cells were then collected by drawing the marrow several times into syringes fitted with an 18-gauge needle. The cells were then pelleted by centrifugation at 1000 rpm for 5 minutes, resuspended in serum-free medium, and counted with a hemocytometer.

Rat tail tendon type I collagen was prepared as described by Nimni et al. Specifically, rat tail tendons were harvested and rinsed with 1×PBS, digested overnight with pepsin (0.5 mg/ml), precipitated two times with 1M NaCl (pH 7.5) and dialyzed into 0.5 M acetic acid, followed by dialysis into 0.001N HCl. The concentration of collagen was determined by a hydroxyproline assay, while its purity was confirmed by 2-D peptide mapping, as described by Benya et al., *Collagen Res* 1:17–26 (1981). Three mg/ml collagen were diluted three times with 3×DMEM to make a 1×collagen solution, whereafter the pH was adjusted to 7.5 and aliquots were stored at 40° C.

Washed cell pellets were suspended in 10 µl serum-free medium and 200 µl neutralized collagen, after which 10 µl recombinant TGFβ1-vWF or control medium was added. The cell/collagen mixtures were then transferred to 24-well tissue culture plates and incubated at 37° C. for 30 minutes until the collagen molecules aggregated into fibrils, thus trapping cells within the collagen gels. 0.5 ml of 0.5% FBS in DMEM medium was then overlayed on the gel, and the cells were incubated at 37° C. for 7 days without changing the medium. After 7 days of serum deprivation, the medium was replaced with D10 medium, which was thereafter changed every 3 days. Seven days after reconstitution with D10 medium, selected cultures were supplemented with osteoinductive agents: $10^{-8}$M dexamethasone, $2.8\times10^{-4}$M ascorbic acid and 10 mM β-glycerol phosphate in D10 medium.

EXAMPLE 5

Transduction of TGFβ1-Selected Cells and Marrow Stromal Cells with β Galactosidase and Factor IX (LIXSNL) Retroviral Vectors The TGFβ1-vWF responsive cells captured within the collagen pads (or on collagen-coated plates) and the human marrow stromal cells selected by differential plating in DMEM-10% FBS (D10) were exposed for two hours to both a β galactosidase vector (G1BgSvNa) and a factor IX vector (LIXSNL) in the presence of 8 µg/ml Polybrene. The names G1BgSvNa and LIXSNL indicate the order of promoter and coding regions (G1 or L=MoMuLV LTR; Bg=β galactosidase cDNA; IX=human factor IX cDNA; Sv or S=SV40 promoter; Na or N=neomycin phosphotransferase gene). The vector titers were 1.3×10⁶ cfu/ml for G1BgSvNa and 1×10⁶cfu/ml for LIXSNL. The LXSNL vector, which contains only the neomycin resistance gene, served as the control vector. The G1BgSvNa and LIXSNL retroviral vectors were provided as PA317 producer cell clones by Genetic Therapy, Inc., Gaithersburg, Md., and Dr. Dusty Miller, University of Washington, Seattle, Wash., respectively.

After forty-eight hours, the collagen pads were fixed with paraformaldehyde and stained with X-gal (β galactosidase) stain to detect cells producing cytoplasmic β galactosidase. The marrow stromal cells transduced with the β galactosidase vector were also stained with X-gal stain before and after G418 selection. The transduction efficiency of stromal cells was determined in transduced, unselected cells by determining the number of blue-staining cells in 300 cells counted. This number was then expressed as the percent of blue-staining cells. See Skotzko M. J., et al., "Retroviral Vector-mediated Gene Transfer of Antisense Cyclin G1 (CYCG1) Inhibits Proliferation of Human Osteogenic Sarcoma Cells," *Cancer Research* 55:5493–5498 (1995). At serial intervals, medium was harvested from the cell cultures transduced with the factor IX and control vectors and stored in aliquots at −70° C. until assayed for factor IX clotting activity and antigen.

Factor IX coagulant activity was measured as described by Gordon E. M., et al., "Characterization of Monoclonal Antibody-purified Factor IX Produced in Human Hepatoma (HepG2) Cell Cultures after Retroviral Vector-Mediated Transfer," *J. Int. Pediatr. Heamtol. Oncol.* 2:185–191, (1995) using a modification of the partial thromboplastin time while the amount of factor IX antigen was measured using a specific radioimmunoassay technique, as described by Gordon E. M., et al., "Expression of Coagulation Factor IX (Christmas factor) in Human Hepatoma (HepG2) Cell Cultures after Retroviral Vector-Mediated Transfer," *Amer. J. Pediatr. Hematol. Oncol.* 15:195–203 (1993). Any significance in differences among groups was tested by analyzing variance. See Dixon W. J., et al., BMDP Statistical Software (Berkley: University of California Press, 1990).

EXAMPLE 6

Transplantation of Murine Mesenchymal Progenitor Cells Transduced with a Factor IX (LIXSNL) Retroviral Vector TGFβ1-responsive cells from bone marrow of 6 week-old, 20 gm, B6CBA immunocompetent mice (Jackson Labs, Barr Harbor, Me.) were captured on collagen-coated, TGFβ1-vWF impregnated plates under serum-poor conditions (DMEM-1% FBS) for 5 days. The cultures were then reconstituted in D10 medium (DMEM-10% FBS). The expanded cultures were transduced on the 7th day with the LIXSNL factor IX vector or LXSNL control vector in the presence of 8 µg/ml Polybrene, and maintained in D10 for two more weeks. On the 21st day, 1×10⁵ cells were infused into the tail vein of mice from the same strain (n=3 for each group). Blood samples were collected every 7 days from the mousers tail for conducting a factor IX antigen assay.

EXAMPLE 7

Reverse-transcriptase-based Polymerase Chain Reaction (RT-PCR) Analysis of the Human Factor IX Transgene in Murine Organs Total RNA was isolated from different organs of the mice treated in Example 6 by the guanidinium isothiocyanate method, as described by Chormczynski P., et al., "Single Step Method of RNA Isolation by Acid Guanidinium Thiocyanate-Phenol-Chloroform Extraction," *Anal. Biochem.* 192:156–59 (1988). The first strand of cDNA from total RNA was synthesized by reverse transcriptase, as described by the Invitrogen cDNA Cycle Kit (Invitrogen, San Diego Calif.), followed by PCR amplification. Each reaction in a 20 μl volume contained 1 μg RNA, 1 μg random primer and 5 units AMV reverse transcriptase.

The RNA and random primers first were heated together at 65° C. to remove their secondary structure and then placed at room temperature for 2 minutes. The subsequent reactions were then carried out in 1×reverse transcriptase buffer comprising 5 mM dNTPs, 4 mM sodium pyrophosphate and 5 units of reverse transcriptase, at 42° C. for 60 minutes. The sample was heated at 95° C. for 2 minutes to denature the RNA-cDNA hybrid. To amplify the human factor IX gene by PCR, primers were designed using the region of the factor IX gene within which a difference occurs between the homology of the amino acid sequences of human and mouse cDNA.

Oligonucleotides used for effecting PCR amplification of the human factor IX sequence were as follows: (707) sense 21-mer 5' ACT CAA GGC ACC CAA TCA TTT 3'; (708) 5' AAC TGT AAT TTT AAC ACC AGT TTC AAC 3'. Additionally, human liver RNA was used as a positive control for the amplification reaction.

The cDNA synthesized from the above reaction was denatured first at 94° C. for 5 minutes, then at 80° C. for 1 minute, followed by 60° C. for 45 seconds (step 1). The sample was then heated at 72° C. for 2 minutes (step 2), followed by heating at 94° C. for 1 minute, 60° C. for 45 seconds, and 72° C. for 10 minutes (step 3). Steps 1 and 2 were performed only once, while step 3 was carried out 30 times. After the reaction was completed, the samples were run on 2.5% agarose gels to visualize the factor IX bands, as demonstrated by FIG. 7.

Accordingly, the above findings demonstrate that TGF XL can be used in a gene therapy protocol, wherein bone marrow-derived cells, preferably pluripotent stem cells, are the desired targets for delivering a gene to a subject.

The disclosures of all patents, patent applications and publications referenced in this specification are specifically incorporated herein by reference in their entirety to the same extent as if each such individual patent, patent application or publication were specifically or individually indicated to be incorporated by reference in its entirety.

What is claimed is:

1. A method for providing a mammal with a therapeutic factor IX protein comprising:

a) capturing TGFβ1-responsive, bone marrow-derived cells under low serum conditions in a collagen matrix impregnated with a TGFβ1 fusion protein comprising a von Willebrand's factor-derived collagen binding site which targets the TGFβ1 protein to the collagen matrix;

b) expanding the captured cells to form differentiated cell colonies;

c) isolating the expanded cells;

d) transducing the expanded cells in vitro with a viral vector comprising a nucleic acid encoding a factor IX protein; and e) introducing the transduced cells into the mammal, wherein the transduced cells express the therapeutic factor IX protein in vivo.

2. The method of claim 1, wherein additional TGFβ1 is provided during the steps (a) and (b).

3. The method of claim 1 and 2, wherein the TGFβ1-responsive, bone marrow-derived cells are stem cells or stromal cells.

4. The method of claim 3, wherein the viral vector is a retroviral vector.

* * * * *

UNITED STATES PATENT AND TRADEMARK OFFICE
CERTIFICATE OF CORRECTION

PATENT NO.    : 6,277,369 B1
DATED         : August 21, 2001
INVENTOR(S)   : W. French Anderson, Frederick L. Hall and Erlinda M. Gordon It is certified that error appears in the above-identified patent and that said Letters Patent is hereby corrected as shown below:

Drawings,
Please substitute the attached sheets 1 of 4 containing FIGs. 1, 2, 3A-3C, 4A-4D, 5A-5D, 6A-6C and FIG. 7.

Signed and Sealed this

Twelfth Day of November, 2002

Attest:

JAMES E. ROGAN
Attesting Officer    Director of the United States Patent and Trademark Office

VWF-TGF-β Fusion protein

Trp-Arg-Glu-Pro-Ser-Phe-Met-Ala-Leu-Ser (HIS)6 — [protease site] — TGF-β1

Protease site

FIG. 1

Legend (DMEM):
- □ 10% FBS
- ◇ 5% FBS
- ○ 3% FBS
- △ 2% FBS
- ▽ 1% FBS

Y-axis: CELL COUNT, $10^4$
X-axis: TIME, DAYS

FIG. 2

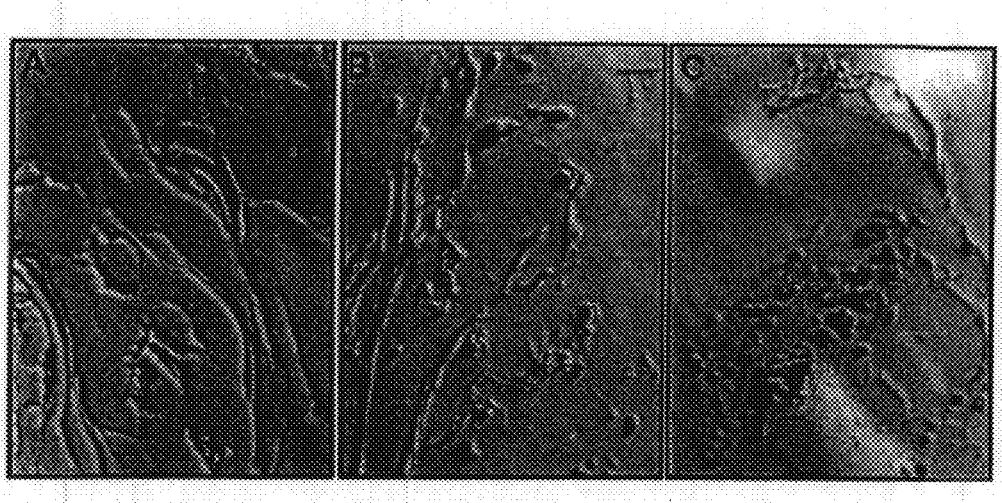
*FIG. 3A*  *FIG. 3B*  *FIG. 3C*
*FIG. 5A*  *FIG. 5B*
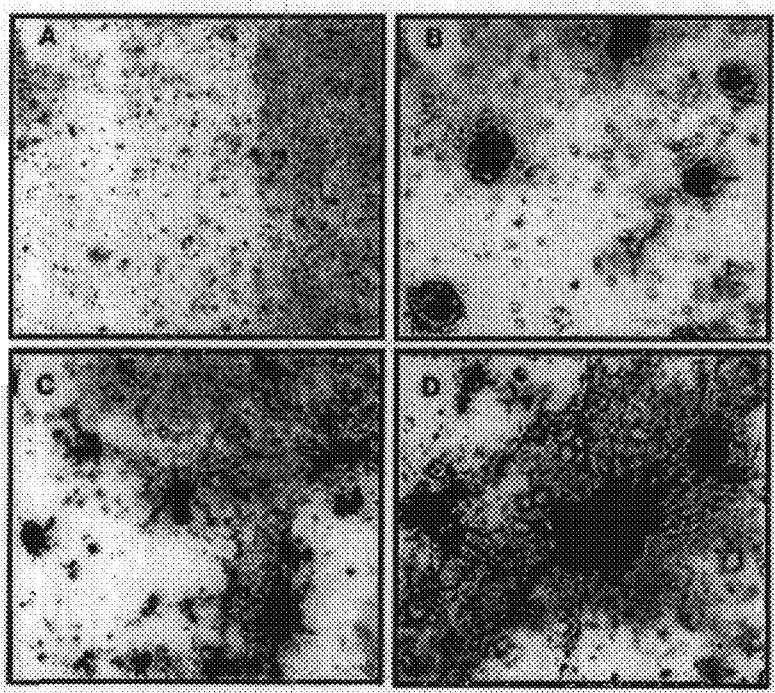
*FIG. 5C*  *FIG. 5D*

Figure 4B:
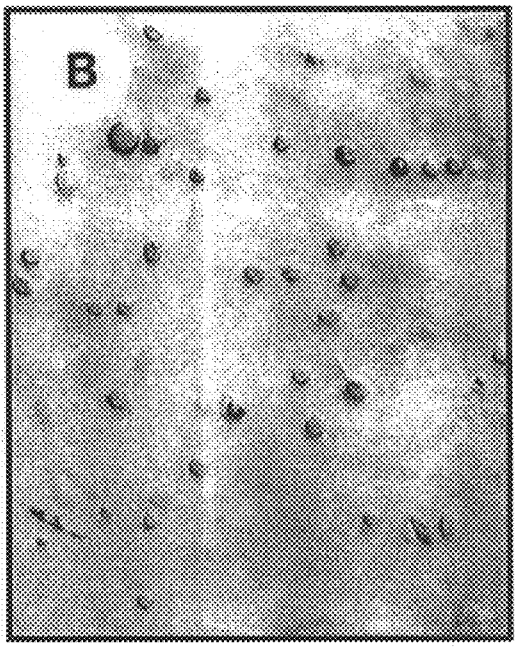
Figure 4C:
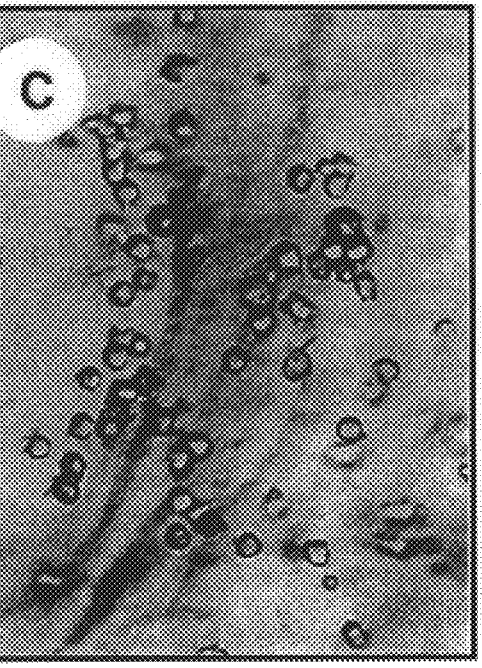
Figure 4D:
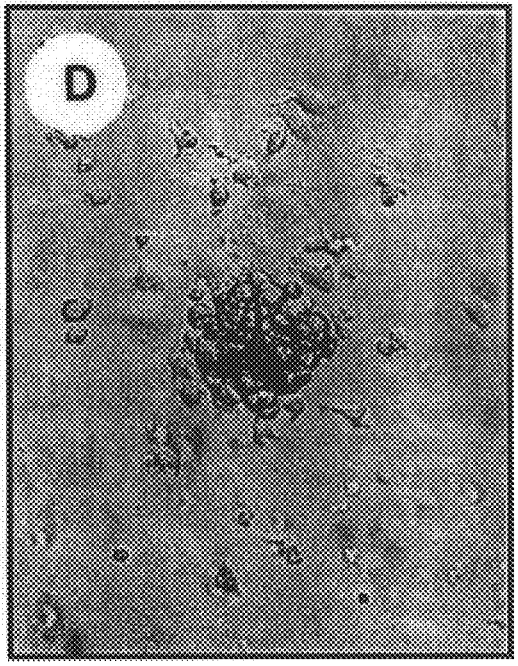

FIG. 4A
FIG. 4B
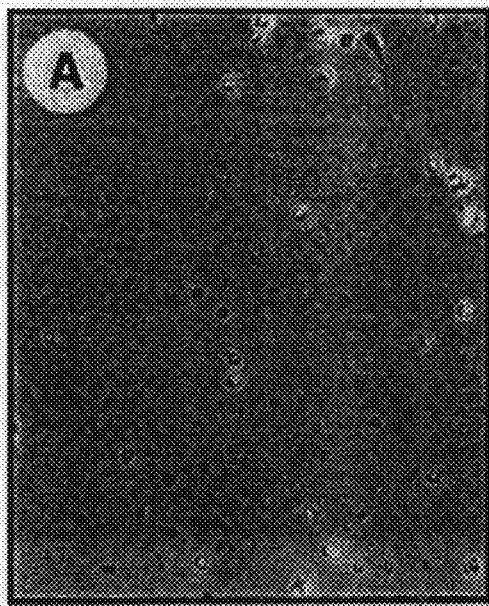
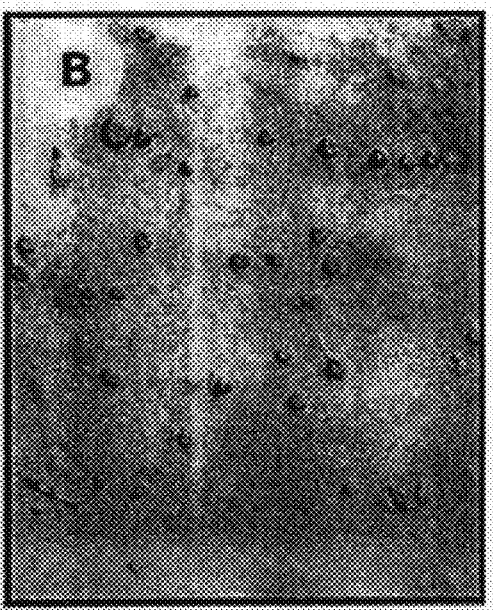
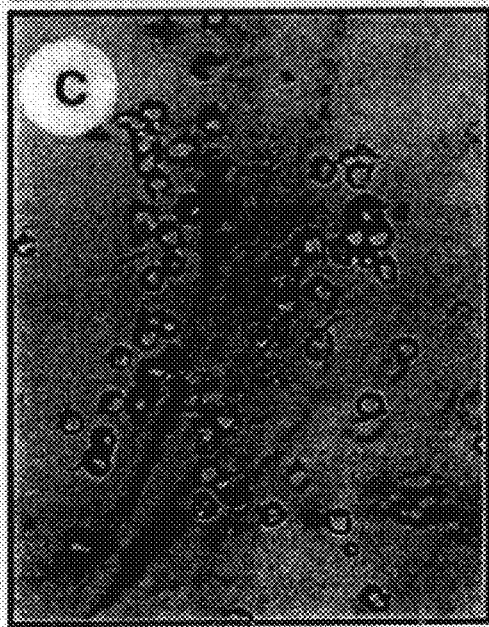
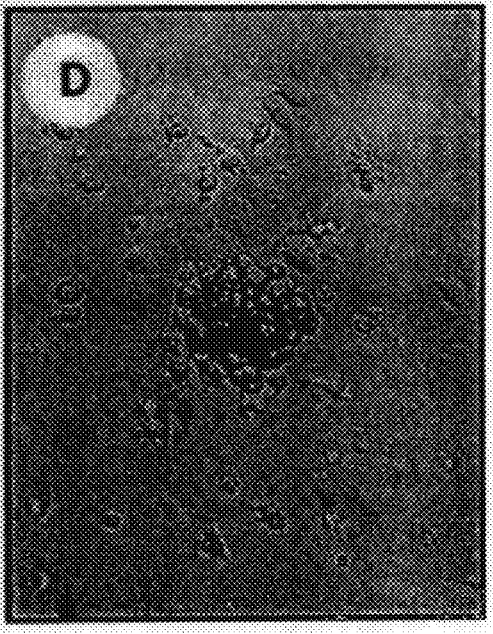
FIG. 4C
FIG. 4D

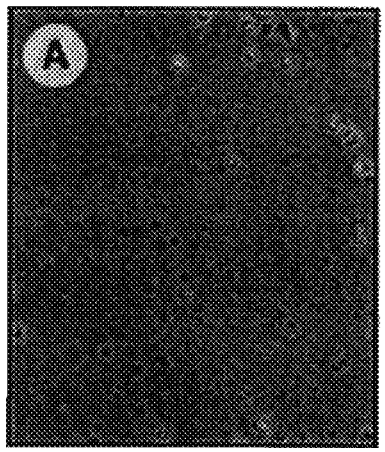 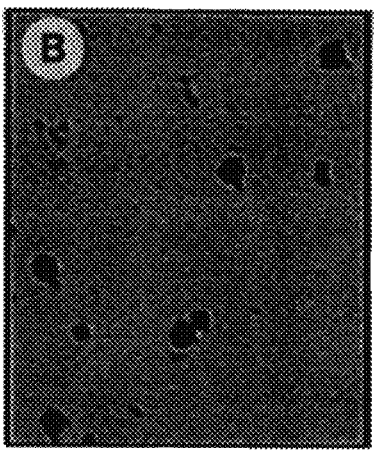 
*FIG. 6A*  *FIG. 6B*  *FIG. 6C*
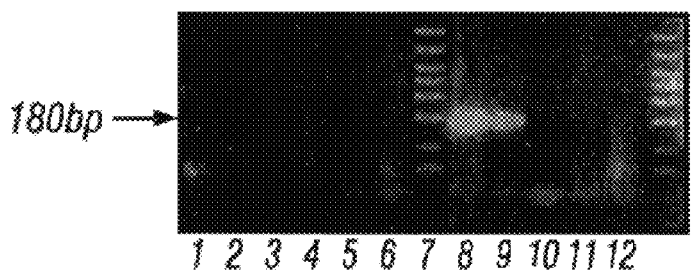
*FIG. 7*